US00PP09012P

United States Patent [19]

Warner

[11] Patent Number: Plant 9,012

[45] Date of Patent: Dec. 13, 1994

[54] CLIMBING MINIATURE ROSE PLANT NAMED CHEWARVEL

[75] Inventor: Christopher H. Warner, Shropshire, England

[73] Assignee: Bear Creek Gardens, Inc., Medford, Oreg.

[21] Appl. No.: 202,512

[22] Filed: Feb. 24, 1994

[51] Int. Cl.[5] ..... A01H 5/00

[52] U.S. Cl. ..... Plt./2

[58] Field of Search ..... Plt. 2, 3, 5, 7.1, 8.2, Plt. 9

U.S. PATENT DOCUMENT

PLT 2176 9/1962 Moore ..... PLT/3

*Primary Examiner*—Howard J. Locker

*Attorney, Agent, or Firm*—Klarquist Sparkman Campbell Leigh & Whinston

[57] ABSTRACT

A climbing miniature rose plant having a vigorous climbing habit of growth, the plant having long climbing shoots from the base that end in a flower cluster and many auxiliary buds along the shoots, which break quickly into short stems that flower, giving a pillar-like plant habit; small, glossy, dark green foliage; small, yellow flowers borne in large clusters; and resistance to powdery mildew and rust.

1 Drawing Sheet

The present invention relates to a new and distinct variety of rose plant of the climbing miniature class which was originated by me by crossing the variety HARpiccolo with an unnamed seedling from a cross of the variety MACel with an unnamed seedling resulting from a cross of the varieties MACba and "Sutter's Gold" (U.S. Plant Pat. No. 885).

The primary objective of this breeding was to produce a new rose variety having the climbing habit of the male parent combined with the small foliage and flowers of the female parent. The objective was substantially achieved, along with other desirable improvements, as evidenced by the following unique combination of characteristics that are outstanding in the new variety and that distinguish it from its parents, as well as from all other varieties of which I am aware:

1. Small, glossy foliage from top to bottom of the plant;
2. Small flowers borne in large clusters from early to late in the season;
3. Upright climbing habit of growth; and
4. Resistance to powdery mildew and rust.

Asexual reproduction of this new variety by budding and by softwood cuttings as performed at Wasco, Calif., and Newport, Shropshire, England, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—HARpiccolo.

*Pollen parent.*—(MACel)× (MACba×"Sutter's Gold" [U.S. Plant Pat. No. 885]).

Classification:

*Botanical.*—Rosa hybrida.

*Commercial.*—Climbing miniature.

FLOWER

Observations made from specimens grown in a garden environment at Somis, Calif., and Newport, Shropshire, England.

Blooming habit: Recurrent.

Bud:

*Size.*—13 mm long when the petals start to unfurl.

*Form.*—The bud form is short, pointed ovoid.

*Color.*—When sepals first divide, bud color is Yellow Group 4B. When half blown, the upper side of the petals are Yellow Group 5B, and the lower side of the petals are Yellow Group 4B.

*Sepals.*—Color: Green Group 138B. Surface texture: Covered in fine hairs. There are three lightly appendaged sepals and two unappendaged sepals with hairy edges.

*Receptacle.*—Color: Green Group 137C. Shape: Funnel. Size: Small (5 mm×5 mm). Surface: Smooth.

*Peduncle.*—Length: Short (4 cm). Surface: Smooth. Color: Medium green. Strength: Stiff, erect, slender.

Bloom:

*Size.*—Small. Average open size is 25 to 38 mm.

*Borne.*—Several together, in pyramidal clusters.

*Stems.*—Long (60 to 76 cm on main stems, and 20 to 25 cm on lateral stems); strong.

*Form.*—When first open: High centered. Permanence: Flattens, outer petals curl back.

*Petalage.*—Number of petals under normal conditions: 20.

*Color.*—The upper side of the petals are Yellow Group 5B. The reverse side of the petals are Yellow Group 4B. The base of the petals is Yellow Group 5A. The major color on the upper side is Yellow Group 5B.

*Variegations.*—None.

*Discoloration.*—The general tonality at the end of the first day: No change. At the end of the third day: Gradual fading of yellow color to Yellow Group 5D. At the same time there is a flush of pink (Red Group 49A) that covers much of the petals' upper surfaces.

*Fragrance.*—Slight, fruity fragrance.

Petals:

*Texture.*—Thick.

*Shape.*—Deltoid.

*Form.*—Tips slightly recurved.

*Arrangement.*—Imbricated, with few petaloids in the center.

*Persistence.*—Drop off cleanly.

*Lastingness.*—On the plant: Fair (5 to 6 days). As a cut flower: Fair (5 to 6 days).

Reproductive Parts:

*Anthers.*—Size: Medium. Quantity: Many. Color: Yellow. Arrangement: Regular around styles.

*Filaments.*—Color: Yellow.

*Pollen.*—Color: Gold yellow.

*Styles.*—Color: Red.

Stigmas.—Color: Greenish white.

Form: Climber.

Growth: Very vigorous, upright, branching. Will grow to 2.5 meters the first year in California. The plant sends up long climbing shoots from the base that end in a flower cluster. The auxiliary buds along this shoot break quickly into 20 to 25 cm stems that flower, giving a novel, pillar-like plant habit.

Foliage: Number of leaflets on normal mid-stem leaves: 5.

*Size.*—Small (76 mm×51 mm).

*Quantity.*—Abundant.

*Color.*—New foliage: Reddish (Greyed Purple 183A). Old foliage: Dark, glossy green (Green Group 139A).

Leaflets:

*Shape.*—Pointed oval.

*Texture.*—Upper side: Leathery, glossy.

*Edge.*—Smooth.

*Serration.*—Single, small.

*Petiole rachis.*—Color: Green.

*Petiole underside.*—Smooth, with occasional prickles.

*Stipules.*—Short, bearded.

*Disease resistance.*—Resistant to mildew and rust under normal growing conditions at Somis, Calif., and Newport, Shropshire, England.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Medium (⅛ inch), hooked downward.

*Color when young.*—Red. Small prickles:

*Quantity.*—On main stalks: None. On laterals: None.

I claim:

1. A new and distinct variety of rose plant of the climbing miniature class, substantially was herein shown and described, characterized particularly as to novelty by the unique combination of its vigorous climbing habit of growth, the plant having long climbing shoots from the base that end in a flower cluster and many auxiliary buds along the shoots, which break quickly into short stems that flower, giving a pillar-like plant habit; small, glossy, dark green, foliage; small, yellow flowers borne in large clusters; and resistance to powdery mildew and rust.

* * * * *

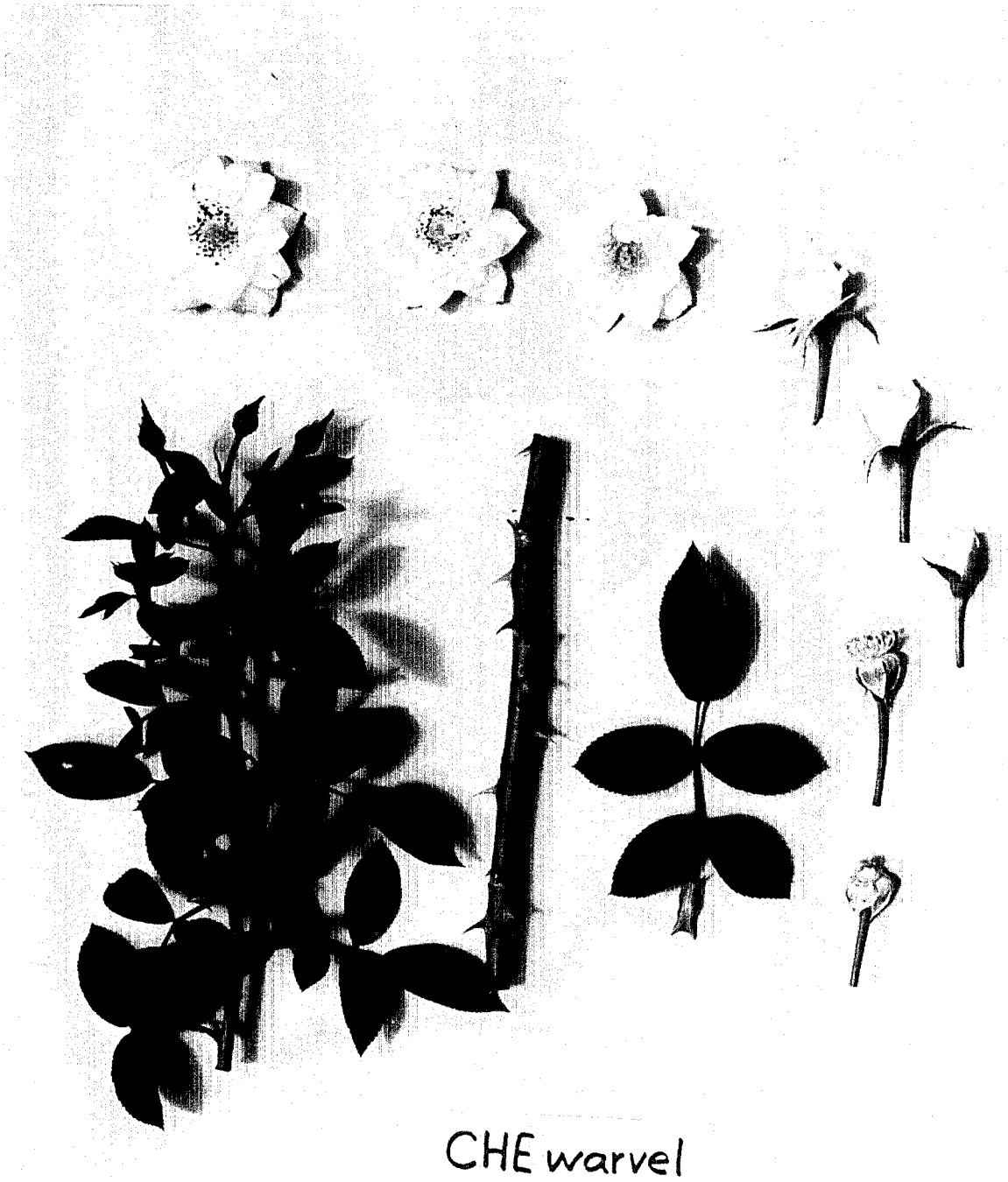
CHE warvel